US010070933B2

(12) United States Patent
Adler et al.

(10) Patent No.: US 10,070,933 B2
(45) Date of Patent: Sep. 11, 2018

(54) CUSTOM PROCEDURE KIT

(75) Inventors: Deborah Adler, New York, NY (US); Kim Haines, Deerfield, IL (US)

(73) Assignee: Medline Industries, Inc., Northfield, IL (US)

(*) Notice: Subject to any disclaimer, the term of this patent is extended or adjusted under 35 U.S.C. 154(b) by 887 days.

(21) Appl. No.: 13/552,741

(22) Filed: Jul. 19, 2012

(65) Prior Publication Data

US 2014/0021087 A1 Jan. 23, 2014

(51) Int. Cl.
*B65D 69/00* (2006.01)
*A61B 50/30* (2016.01)
*A61B 90/92* (2016.01)

(52) U.S. Cl.
CPC ............ *A61B 50/30* (2016.02); *A61B 90/92* (2016.02); *A61B 2050/3011* (2016.02); *A61B 2050/3012* (2016.02); *A61B 2050/3015* (2016.02); *A61B 2050/314* (2016.02)

(58) Field of Classification Search
CPC .......... A61B 19/026; A61B 2019/0267; A61B 2019/444; A61B 2019/0282; A61B 2019/0281; A61B 2019/0286; A61B 90/92; A61B 50/30; A61B 2050/314; A61B 2050/3011; A61B 2050/3012; A61B 2050/3015
USPC .......... 206/232, 363–365, 438, 459.1, 459.5, 206/534, 570–572, 803; 383/20, 21, 25
See application file for complete search history.

(56) References Cited

U.S. PATENT DOCUMENTS 3,650,393 A * 3/1972 Reiss et al. .................. 206/571
4,091,927 A * 5/1978 Lunsford .................... 206/459.5
4,523,679 A * 6/1985 Paikoff et al. ................ 206/570
4,573,203 A * 2/1986 Peppiatt ................ B65D 33/10
                                                            383/29
4,595,102 A    6/1986 Cianci et al.
5,117,981 A * 6/1992 Crawford et al. ............ 206/570
5,170,804 A * 12/1992 Glassman ...................... 128/849
5,318,543 A * 6/1994 Ross et al. .................... 206/571
5,931,303 A * 8/1999 Salvadori ...................... 206/570
(Continued)

FOREIGN PATENT DOCUMENTS

JP          3062992 U      10/1999
JP       2005506110 A       3/2005
(Continued)

OTHER PUBLICATIONS

International Search Report and Written Opinion of the International Searching Authority dated Oct. 18, 2013 in PCT Patent Application No. PCT/US 2013/049091.
Heathcare Professional's Guide to Scanning and Mobility, Data Capture Solutions for Healthcare Applications, Honeywell International Inc., 2010 (online).
(Continued)

*Primary Examiner* — Luan K Bui
(74) *Attorney, Agent, or Firm* — Fitch, Even, Tabin & Flannery LLP (57) ABSTRACT

A custom procedure kit is provided, which comprises a plurality of medical-procedure tools and a cover that is wrapped around the plurality of medical-procedure tools to form wrapped tools. An outer container is fully disposed about the wrapped tools, and at least one sheet is disposed between the outer container and the wrapped tools. The sheet includes a listing of the plurality of medical-procedure tools and, for at least some of the medical-procedure tools, an unselected end-user selectable field.

25 Claims, 7 Drawing Sheets

(56) References Cited

U.S. PATENT DOCUMENTS

| | | |
|---|---|---|
| 7,802,313 B2 | 9/2010 | Czajka |
| 7,828,148 B2* | 11/2010 | Gibson .................. 206/534 |
| 2003/0214129 A1* | 11/2003 | Adler ..................... 283/81 |
| 2005/0029156 A1* | 2/2005 | Girzaitis ................ 206/570 |
| 2005/0183982 A1* | 8/2005 | Giewercer ............. 206/534 |
| 2005/0241986 A1* | 11/2005 | Massengale et al. ..... 206/570 |
| 2006/0241868 A1 | 10/2006 | Sun et al. |
| 2007/0084742 A1 | 4/2007 | Miller et al. |
| 2008/0196304 A1* | 8/2008 | Pope ..................... 206/597 |
| 2009/0281464 A1 | 11/2009 | Cioanta et al. |
| 2010/0078351 A1* | 4/2010 | Sherrill ................ 206/570 |
| 2010/0311026 A1* | 12/2010 | Tomes ............ A61M 25/002 206/571 |
| 2011/0232234 A1* | 9/2011 | Lockwood ........ A61M 25/00 53/443 |
| 2011/0233079 A1* | 9/2011 | Macinnes ........ A61M 25/002 206/232 |
| 2011/0313894 A1 | 12/2011 | Dye et al. |

FOREIGN PATENT DOCUMENTS

| | | |
|---|---|---|
| WO | 02/083021 A1 | 10/2002 |
| WO | 2005027767 A1 | 3/2005 |
| WO | 2012092598 A2 | 7/2012 |
| WO | 2012164201 A1 | 12/2012 |

OTHER PUBLICATIONS

Preventing Allergic Reactions to Natural Rubber Latex in the Workplace, Latex Alert, National Institute of Occupational Safety and Health (NIOSH) CS-271 Apr. 1999 (online).

Gimenez Burgos, R.; Examiner; Extended European Search Report for European Patent Application No. 13820233.8 dated Mar. 1, 2016; 9 pages.

Japanese Office Action from Japanese Patent Application No. 2015-523109 dated Jun. 13, 2017, with English translation; 9 pages.

Williams, Timothy; Examination Report from Australian Patent Application No. 2017279699 dated Jun. 21, 2018; 5 pages.

* cited by examiner

CUSTOM PROCEDURE KIT

TECHNICAL FIELD

This invention relates generally to custom procedure kits for use in medical procedures.

BACKGROUND

Many medical service providers such as doctors, nurses, and surgeons use procedure kits, often referred to as surgical packs, surgical kits, and/or sterile procedure trays, that contain a variety of tools and/or implements useful for a particular surgical procedure. The tools are generally disposable, and may include supplies such as covers, gowns, towels, gauze, tubing, syringes, and so forth. As one example, an appendectomy surgical pack for a particular hospital may include twenty or thirty tools specified by the hospital for performing that procedure. When an appendectomy is scheduled, one of the appendectomy-specific surgical kits is retrieved from the stock room and is delivered to the operating room. The surgeon and nurses generally use at least some of the tools during the procedure and then dispose of all the tools after the procedure.

Many such surgical packs are customized and packed to customers' specific requirements. Different customers may require different components for each procedure. For example, one hospital may suture a wound with degradable suture material, while another may prefer non-degradable suture material, and so forth. Some manufacturers offer tens of thousands of different types of surgical packs.

One problem associated with surgical packs (regardless of whether they are a generic offering or a customized offering) is the potential for generating excess waste if, for example, a surgical pack intended for one particular procedure is erroneously opened for a different type of procedure or the surgical pack contains tools that are routinely unused by a given service provider for whatever reason.

Additionally, while surgical packs for routine procedures may include only twenty to thirty items, some surgical packs can include as many as two hundred tools. Thus, many surgical packs tend to be rather large and bulky, making it difficult for a person to manage one or more surgical packs while transporting the pack(s) from storage to the operating room. The applicant has determined that existing approaches in these regards leave room for considerable improvement.

BRIEF DESCRIPTION OF THE DRAWINGS

The above needs are at least partially met through provision of the custom procedure kit described in the following detailed description, particularly when studied in conjunction with the drawings, wherein.

Common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments comprise a custom procedure kit. As used herein, "custom" refers to the fact that the contents of a kit may be selected and/or modified based on a number of variables, including the intended genre of medical procedure, the desired barrier protection level for the procedure, and/or the specific preferences of the hospital/surgical center and/or end user. The kit comprises a plurality of medical-procedure tools and a cover that is wrapped around the plurality of medical-procedure tools to form wrapped tools. An outer container may be fully disposed about the wrapped tools, and at least one sheet may be disposed between the outer container and the wrapped tools. The sheet includes a listing of the plurality of medical-procedure tools and, for at least some of the medical-procedure tools, an unselected end-user selectable field.

The sheet may further include text to identify the purpose of the unselected end-user selectable fields. By one approach, the purpose is to identify specific medical-procedure tools that went unused during a medical procedure that used other medical-procedure tools in the kit.

The kit may include various features to facilitate selection of an appropriate kit for a given procedure and physical transport of the kit to the operating room. By one approach, at least one of the outer container and the sheet further includes at least one marker, wherein the marker includes a color that indicates a particular genre of medical procedure to which the plurality of medical-procedure tools specifically relate. Pursuant to another approach, the marker includes a color that indicates a barrier protection level of at least one of the plurality of medical-procedure tools within the kit. By another approach, the outer container includes a hand-graspable handle and/or an arm-receiving sleeve.

These teachings are highly flexible and scalable in practice and can serve to greatly leverage a wide variety of existing custom procedure kits and/or surgical packs. Such a custom procedure kit can also greatly facilitate prompting and ensuring selection of an appropriate kit containing pertinent medical-procedure tools for a particular genre of medical procedure. This can advantageously reduce costs and minimize waste associated with erroneously opened kits and kits containing unnecessary tools.

These and other benefits may become clearer upon making a thorough review and study of the following detailed description. Referring now to the drawings, various illustrative custom procedure kits that are compatible with many of these teachings will be presented.

Figure 1:
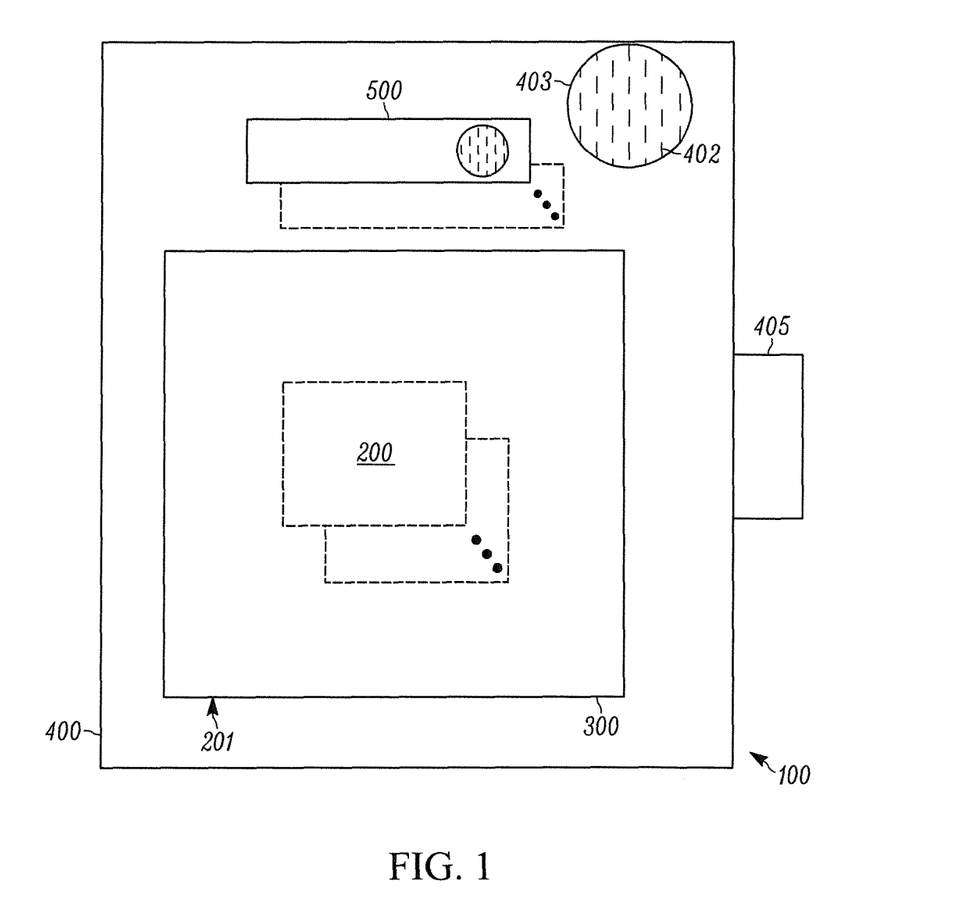
FIG. 1 comprises a schematic view of a kit configured in accordance with various embodiments of the invention.
Figure 2:
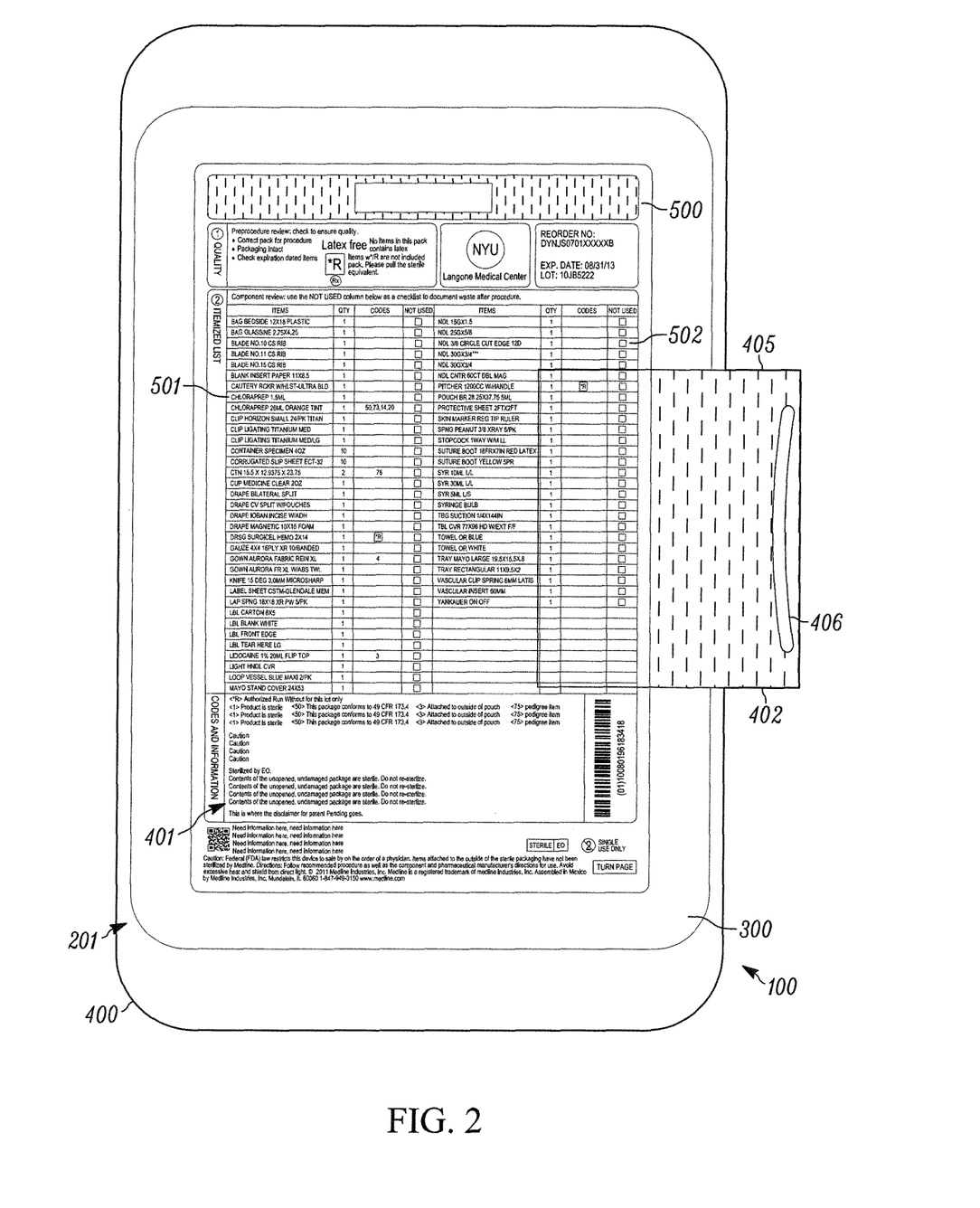
FIG. 2 comprises a front-elevation view of a kit configured in accordance with various embodiments of the invention.
Figure 3:
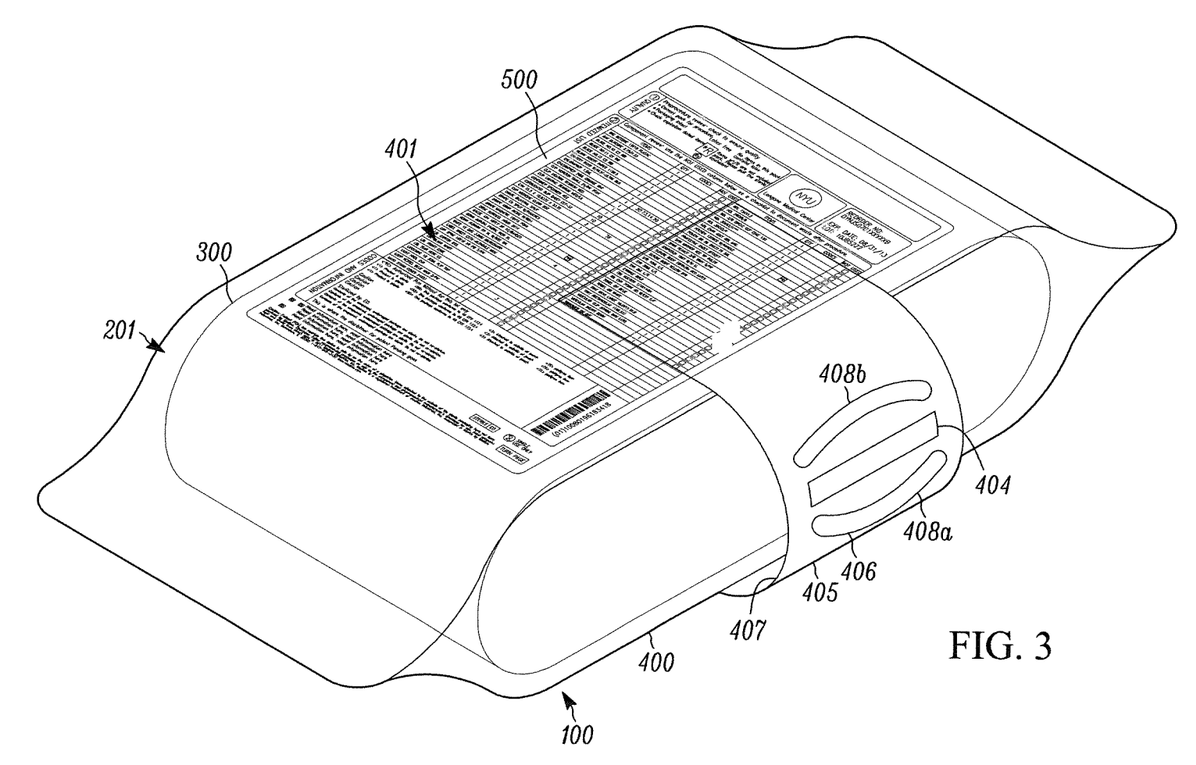
FIG. 3 comprises a perspective view of a kit configured in accordance with various embodiments of the invention.

With reference to FIGS. 1-3, by one approach, the kit 100 includes a plurality of medical-procedure tools 200, a cover 300 that is wrapped around the plurality of medical-procedure tools 200 to form wrapped tools 201, an outer container 400 fully disposed about the wrapped tools 201, and at least one sheet 500 disposed between the outer container 400 and the wrapped tools 201.

As will be readily understood by those of ordinary skill in the art, as used herein, "medical-procedure tools" refers broadly to items useful during a medical procedure. It may include, but is not limited to, items such as instruments, garments, and any number of miscellaneous items. Examples of medical-procedure tools 200 that can be included in the kit 100 include tubing, trays, bandaging materials, scalpels, syringes, needle and blade disposal devices, drapes, clamps, suturing implements, disinfectants, antibiotic creams and lotions, masks, gloves, and so forth. Generally, the plurality of medical-procedure tools 200 include at least one operating room towel, gown, drape, suction tubing, and suction tip. Often, the plurality of medical-procedure tools 200 also include at least one plastic container, syringe, needle, and surgical implement.

The kit 100 may be customized for a particular genre of medical procedure and/or in accordance with the preferences of a particular hospital/surgical center and/or end user. As such, it will be clear to those of ordinary skill in the art that medical-procedure tools 200 other than or in addition to the examples provided above may be included in the kit 100 depending on the genre of medical procedure for which it is customized and/or specific preferences of the hospital/surgical center and/or end user.

By one approach, the kit 100 is disposable. That is, each item within the kit 100, including each of the medical-procedure tools 200 is intended to be used during a procedure and then discarded. Alternatively, one or more items in the kit 100 may be reusable.

By one approach, one or more of the medical-procedure tools 200 within the kit 100 is sterile, having undergone a sterilization process during manufacture of the kit 100. For example, in one form, some of the medical-procedure tools 200 are sterile while others are non-sterile. In other embodiments, all of the medical-procedure tools 200 in the kit 100 may be sterile or non-sterile.

With reference again to FIGS. 1-3, the medical-procedure tools 200 are wrapped with a cover 300 to form wrapped tools 201. The cover 300 can be formed of any of a variety of types of material such as plastic, cotton, linen, paper, and the like, and combinations thereof. By one approach, the cover 300 is a central sterile reprocessing (CSR) wrap such as is widely used by medical professionals in a variety of settings.

In one embodiment the cover 300 is wrapped about the kit 100 for sealing and preventing unwanted debris from contaminating the kit 100. The cover 300 can be correspondingly unfolded to open and reveal the kit 100. The cover 300 can take different sizes and shapes. In the illustrative embodiment, the cover 300 is sufficiently large that it can be wrapped around the kit so as to fully enclose the kit 100. In another form, the cover 300 is sufficiently large that it can be fully wrapped around the kit 100 multiple times.

In some embodiments, the cover 300 may itself be used in the medical procedure. By one approach, the cover 300 comprises a patient support surface cover. In one form, at least one side of the patient support surface cover is sterile. For example, in one form, the inside surface of the cover 300 facing the medical procedure tools 200 is sterile.

By another approach, the cover 300 can be used to cover a surface across which the contents of the kit 100 can be spread. In applications where an inside surface of the cover 300 facing the medical procedure tools 200 is sterile, the cover 300 can be used to provide a sterile field atop which the contents of the kit 100 can be placed for unloading and subsequent use during the medical procedure.

With reference again to FIGS. 1-3, the outer container 400 is fully disposed about the wrapped tools 201. As best illustrated in FIG. 2, by one approach, the outer container 400 has at least one portion 401 that is at least substantially transparent, wherein the sheet 500 is disposed so as to be visible through the at least one portion 401 that is at least substantially transparent. By another approach, the outer container 400 is comprised of plastic sheeting. In one form, the outer container 400 is sized to fit closely around the wrapped tools 201. In such a case, the outer container 400 can assist in securing the position of sheet 500 between the wrapped tools 201 and outer container 400 thereby promoting readability of the sheet 500.

Figure 4:
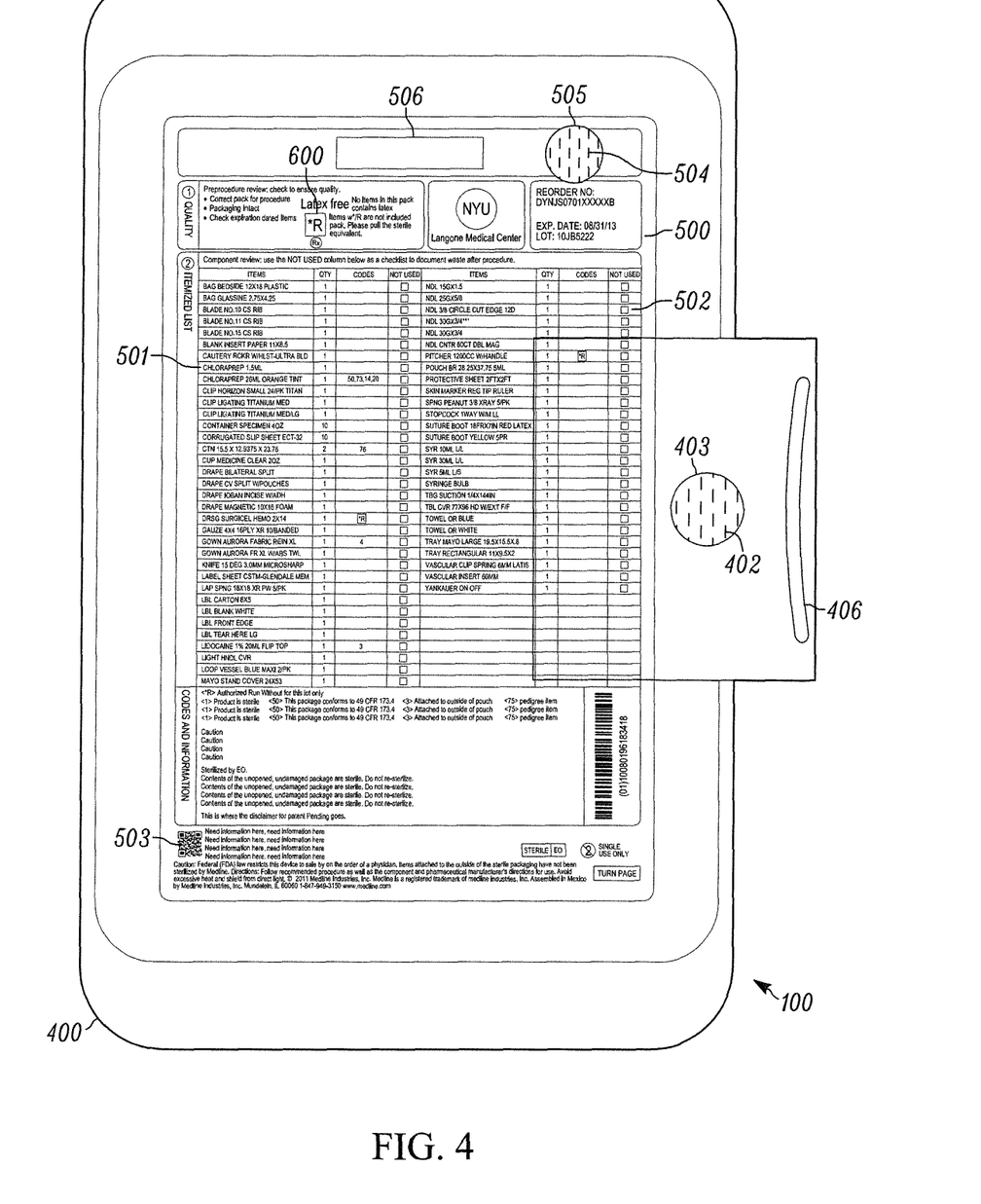
FIG. 4 comprises a front-elevation view of a kit configured in accordance with various embodiments of the invention.

As depicted in FIGS. 1-3, to facilitate identification and selection of an appropriate kit 100, the outer container 400 preferably includes a color 402 that indicates a particular genre of medical procedure to which the plurality of medical-procedure tools 200 specifically relate. In one form, the color 402 can be integral with the outer container, for example, a portion of the outer container may include a colored plastic material. As illustrated in FIG. 4, in another form, the outer container 400 may include at least one marker 403, for example, a sticker or label affixed to the outer container 400 wherein the marker 403 includes the color 402.

By another approach, the color 402 indicates a barrier protection level of at least one of the plurality of medical-procedure tools 200 within the kit 100, for example, a surgical gown, drape, or mask. The barrier protection level designates the ability of the item to protect against the penetration of body fluids and infectious materials. Barrier efficacy is recognized as important in helping to protect patients and health care personnel and to prevent the transmission of infectious materials.

One organization that has established a standard for barrier protection levels is the Association for the Advancement of Medical Instrumentation ("AAMI"). The AAMI standard helps to preserve the sterile field and protect health care workers during surgery and other health care procedures during which exposure to blood, body fluids and other potential infectious material might occur. This AAMI standard establishes a system of classification and associated minimum requirements for protective apparel such as gowns and drapes used in health care facilities based on their liquid barrier performance.

As will be readily understood by those of ordinary skill in the art, the word "color" refers herein to a visually perceptible property deriving from a spectrum of light including the categories of red, blue, yellow, etc. as well as categories of achromatic colors, such as white, black, and gray. The depiction of any specific color in the figures is for illustration only.

In accordance with yet another approach, as depicted, for example, in FIG. 3, the outer container 400 further includes text 404 to indicate the particular genre of medical procedure to which the kit specifically relates.

Figure 5:
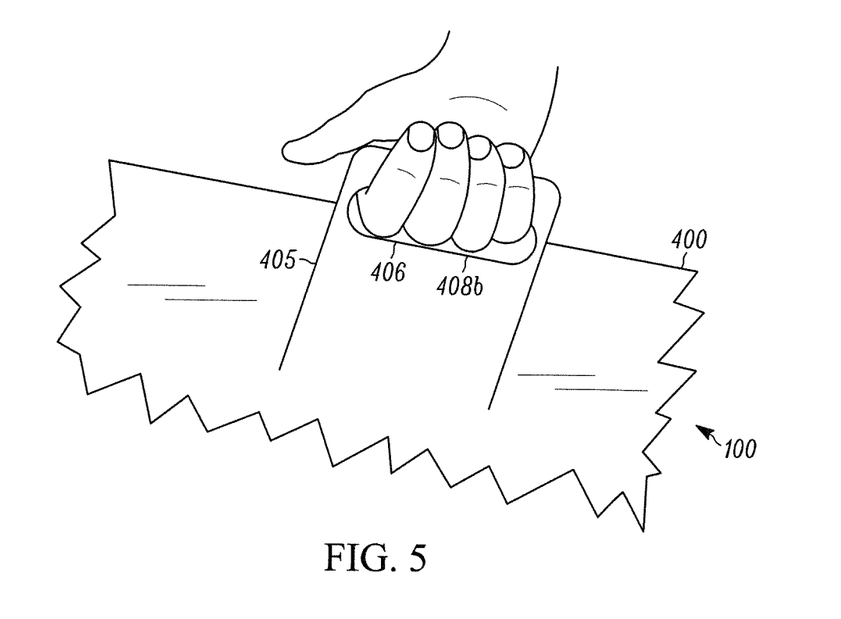
FIG. 5 comprises a perspective partial view of a kit as configured in accordance with various embodiments of the invention.
Figure 6:
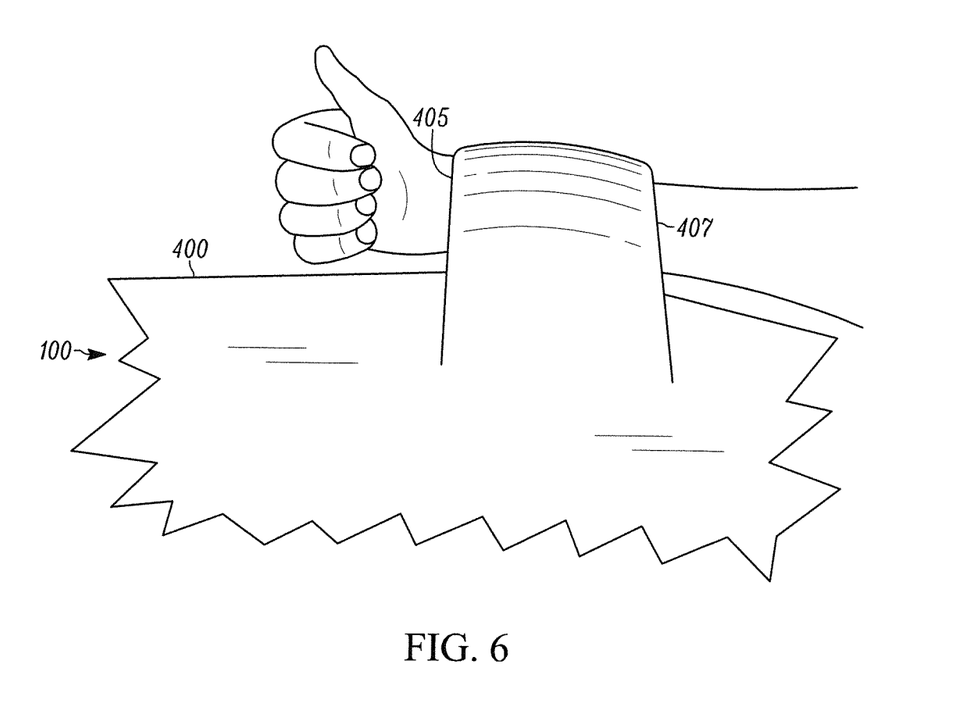
FIG. 6 comprises a perspective partial view of a kit as configured in accordance with various embodiments of the invention.

In accordance with another aspect, the outer container 400 includes a strap or handle 405 to facilitate physically transporting the 100 kit from storage to the operating room. With reference to FIG. 5, in one form, the outer container 400 includes a hand-graspable handle 406. As shown in FIG. 6, in another form, the outer container 400 includes an arm-receiving sleeve 407. In yet another form, as illustrated in FIG. 3, the hand-graspable handle 406 is formed in the arm-receiving sleeve 407. As illustrated, for example, in FIG. 3, the hand-graspable handle 406 may include a pair of voids 408 *a,b* through which a person can place the fingers of one hand so as to grasp the hand-graspable handle 406 in a manner such as illustrated in FIG. 5. In one form, the pair of voids 408 *a,b* are curved with opposing concave portions. In yet another form, shown, for example, in FIG, 2, the aforementioned color 402 and/or text 404 may be incorporated on at least a portion of the handle 405 so as to allow the kits to be easily identified when they are placed on shelves.

Figure 7:
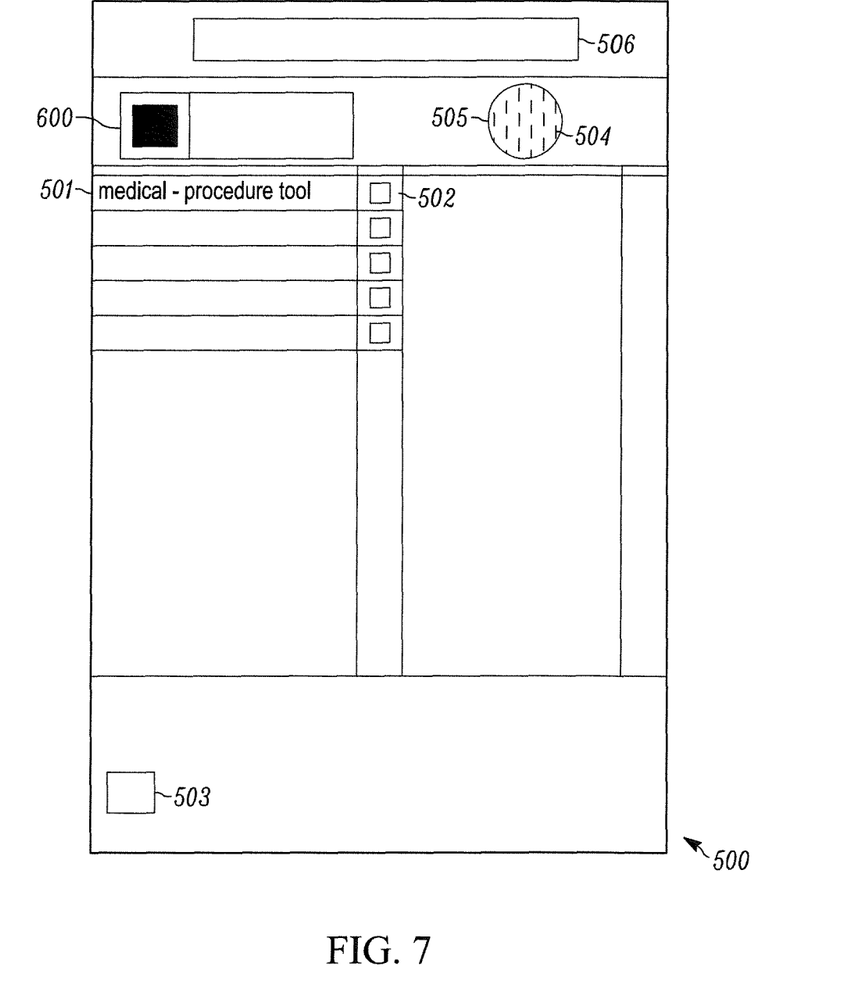
FIG. 7 comprises a schematic view of a sheet configured in accordance with various embodiments of the invention.
Figure 8:
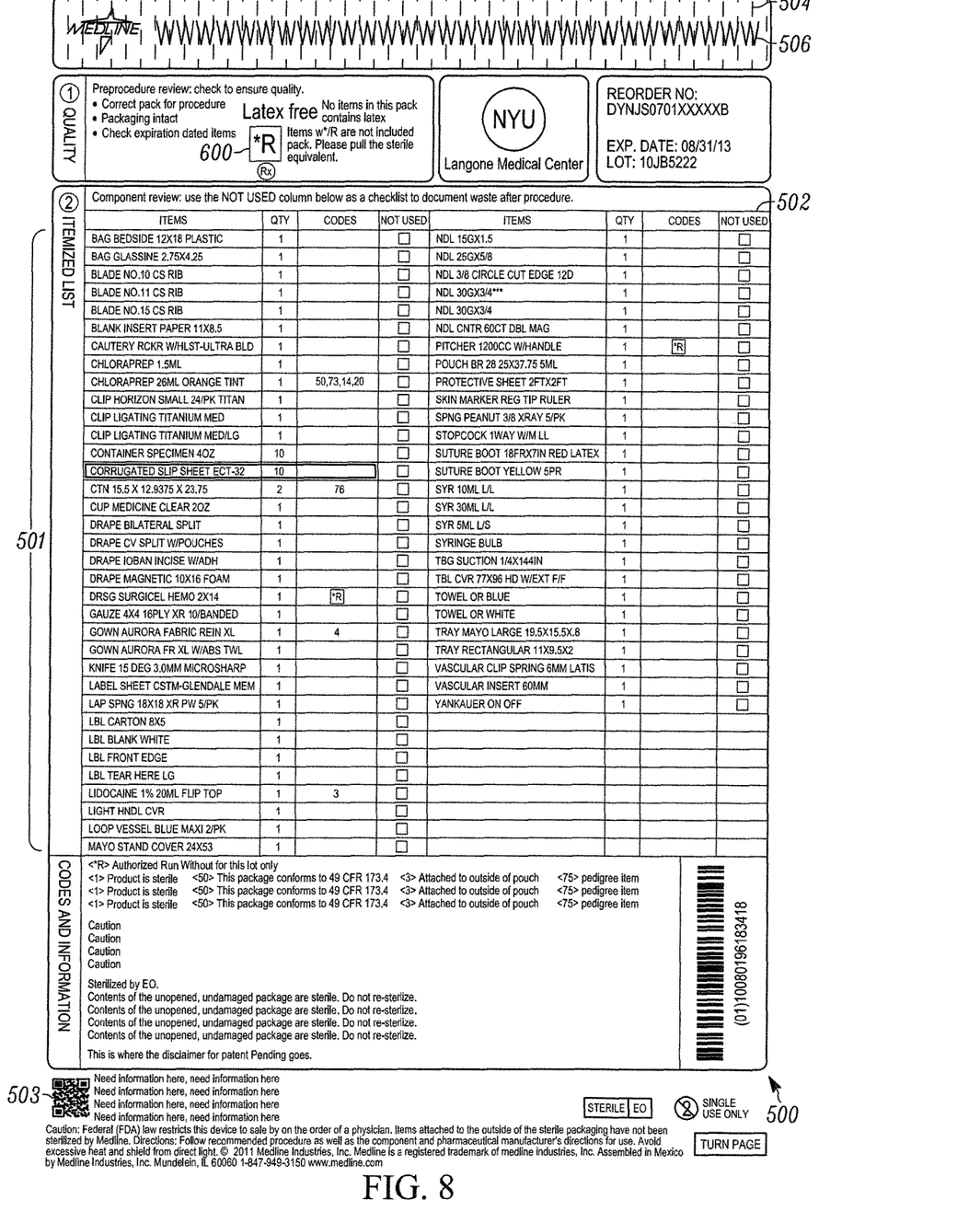
FIG. 8 comprises front a view of a sheet configured in accordance with various embodiments of the invention.

FIGS. 1 and 2, the kit 100 further includes at least one sheet 500 disposed between the outer cover 400 and the wrapped tools 201. This sheet 500 can be comprised of any suitable material such as paper or plastic. By one approach the sheet 500 is flexible and will readily conform, for example, to the shape of the wrapped tools 201. The size of the sheet 500 can vary as needed. The present teachings will also accommodate utilizing more than one sheet 500 in order to accommodate, for example, a greater quantity of content. As illustrated in FIGS. 7 and 8, the sheet 500 includes a listing 501 of the plurality of medical-procedure tools 200 included within the kit 100. The listing 501 may also include the quantity of each type of medical-procedure tool 200 included in the kit 100.

As depicted, for example, in FIGS. 7 and 8, by one approach, the listing 501 includes an unselected end-user selectable field 502 for at least some of the listed medical-procedure tools 200. In one form, the listing 501 includes the unselected end-user selectable field 502 for each of the listed medical-procedure tools 200.

The unselected end-user selectable field 502 can take any suitable form allowing the end-user to select the field. In one illustrated form, the unselected end-user selectable field 502 comprises an unchecked checkbox. As will be readily understood by those of ordinary skill in the art, as used herein "checkbox" refer broadly to shapes in addition to boxes or squares, including for example, circles, ovals, rectangles, etc. In other forms, the unselected end-user selectable field 502 may include, for example, a line or simply a space so long as the purpose of that field 502 in these regards is evident. The end-user selectable field 502 may include a color or marker to highlight or otherwise draw the end-user's attention to the field.

By yet another approach, the listing 500 further includes at least one medical-procedure tool that is not included in the kit 100. The at least one medical-procedure tool 200 that is provided in the listing 501 but not included in the kit 100 may, for example, be an off-the-shelf sterile or non-sterile item that may be routinely used during the particular genre of medical procedure or by the particular hospital/surgical center and/or end-user. In one form, the sheet 500 further includes an unselected end-user selectable field 502 for at least some of the medical-procedure tools that are identified in the listing 501 as not included in the kit 100. In another form, the listing 501 includes an indication that at least one of the listed medical procedure tools 200 is not included in the kit 100.

In another form, the sheet 500 further includes text to identify the purpose of the unselected end-user selectable field 502. By one approach, the purpose of the unselected end-user selectable field 502 is to identify specific medical-procedure tools 200 that went unused during a medical procedure that used other medical-procedure tools 200 in the kit 100.

The end-user selectable field 502 can advantageously be used to capture continuously updated and current data regarding the utilization or non-utilization of any medical-procedure tools 200 included in a kit 100 and any separate, off-the-shelf products that are routinely added during a medical procedure. As the state of a medical practice is continually changing—with surgeons and staff joining and/or leaving, procedures being modified and new procedures being provided—it can be useful to capture this component utilization data on a consistent and continuous basis. The end-user selectable field 502 of the sheet 500 facilitates just that.

By one approach, at the end of the medical procedure, the end-user or other person selects the end-user selectable field 502 of any of medical-procedure tools 200 provided on the listing 501 that was not used during the procedure. The end-user may also write in on the sheet 500 any additional components that were added off-the-shelf during the procedure. The completed sheets (and/or the data entered thereon) can be captured and collected physically or electronically and utilized to further customize the kit 100, for example, by excluding certain medical-procedure tools 200 or adding new tools to the kit 100.

By one approach, illustrated, for example, in FIGS. 7 and 8, the sheet 500 further includes an optical code 503 such as, for example, a universal product code (UPC) barcode or a quick response (QR) code. The optical code 503 preferably contains, at least in part, a network address. The network address may correspond to a facility or service to receive information regarding end-user selections that have been made as regards the end-user selectable fields 502.

As illustrated in FIGS. 7 and 8, by another approach, the sheet 500 further includes a color-based legend 600 as regards at least one caution as pertains to usage of at least one of the plurality of medical-procedure tools 200, wherein the color as corresponds to the color-based legend 600 highlights corresponding ones of the listed medical-procedure tools 200. By one approach, the caution reflected by the color-based legend 600 comprises a presence of latex.

As shown in FIGS. 7 and 8, for example, by another approach, the sheet 500 includes coloring 504 that matches the color 402 of the outer container. As with the color 402 of the outer container 400, the sheet 500 coloring 504 may be integral with the sheet, as provided, for example, by way of colored paper or ink, or the coloring 504 may be provided via a marker 505, for example, a sticker or label, affixed to the sheet 500. By yet another approach, the sheet may also include a text 506 to indicate the particular genre of medical procedure.

These teachings are highly flexible in practice. As one example, the listing 501 of the sheet 500 can vary in length depending on the number of medical-procedure tools 200 included in the kit 100. Likewise, the medical-procedure tools 200 themselves can vary in quantity and type based on the end-users' preferences.

Additionally, these teachings are well suited to prompting and ensuring selection of an appropriate kit 100 containing pertinent medical-procedure tools 200 for a particular genre of medical procedure. Such an approach can advantageously reduce costs and minimize waste associated with erroneously opened kits and kits containing superfluous tools.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A kit comprising:
a plurality of medical-procedure tools;
a cover that is wrapped around the plurality of medical-procedure tools to form wrapped tools;
an outer container fully disposed about the wrapped tools, the outer container having at least one portion that is at least substantially transparent;
at least one sheet disposed between the outer container and the wrapped tools, the at least one sheet being disposed so as to be visible through the at least one portion of the outer container that is at least substantially transparent, the at least one sheet including a listing of the plurality of medical-procedure tools and, for at least some of the medical-procedure tools, an unselected end-user selectable field; and
a handle having at least one portion that is transparent, the handle being disposed on the outer container such that at least a portion of the at least one sheet is visible through the portion of the outer container that is at least substantially transparent and through the portion of the handle that is transparent and wherein the handle comprises an arm-receiving sleeve, wherein the arm-receiving sleeve includes a pair of voids formed therethrough that are configured to receive a user's fingers so as to grasp the handle via the voids.

2. The kit of claim 1 wherein the plurality of medical-procedure tools relate specifically to a particular genre of medical procedure.

3. The kit of claim 1 wherein the plurality of medical-procedure tools include at least one:
operating room towel;
gown;
drape;
suction tubing;
suction tip.

4. The kit of claim 3 wherein the plurality of medical-procedure tools includes at least one of:
plastic container;
syringe;
needle;
surgical implement.

5. The kit of claim 1 wherein the cover comprises a patient support surface cover.

6. The kit of claim 5 wherein at least one side of the patient support surface cover is sterile.

7. The kit of claim 6 wherein at least some of the plurality of medical-procedure tools are sterile.

8. The kit of claim 1 wherein the outer container is comprised of plastic sheeting.

9. The kit of claim 1 wherein the outer container includes a color that indicates a particular genre of medical procedure to which the plurality of medical-procedure tools specifically relate.

10. The kit of claim 9 wherein the outer container further includes text to further indicate the particular genre of medical procedure.

11. The kit of claim 9 wherein the sheet includes coloring that matches the color.

12. The kit of claim 1 wherein at least one of the outer container and the sheet further includes at least one marker, wherein the marker includes a color that indicates a particular genre of medical procedure to which the plurality of medical-procedure tools specifically relate.

13. The kit of claim 1 wherein at least one of the outer container and the sheet further includes at least one marker, wherein the marker includes a color that indicates a barrier protection level of at least one of the plurality of medical-procedure tools.

14. The kit of claim 1 wherein the pair of voids are curved in shape.

15. The kit of claim 14 wherein the pair of voids are curved in shape with opposing concave portions.

16. The kit of claim 1 wherein the listing of the plurality of medical-procedure tools includes, for each of the medical-procedure tools, the unselected end-user selectable field.

17. The kit of claim 1 wherein the unselected end-user selectable field comprises an unchecked checkbox.

18. The kit of claim 1 wherein the sheet further includes text to identify the purpose of the unselected end-user selectable fields.

19. The kit of claim 18 wherein the purpose is to identify specific medical-procedure tools that went unused during a medical procedure that used other medical-procedure tools in the kit.

20. The kit of claim 1 wherein the sheet further includes a color-based legend as regards at least one caution as pertains to usage of at least one of the plurality of medical-procedure tools, wherein a color as corresponds to the color-based legend highlights corresponding ones of the listed medical-procedure tools.

21. The kit of claim 20 wherein the caution comprises a presence of latex.

22. The kit of claim 1 wherein the listing further includes at least one medical-procedure tool that is not included in the kit.

23. The kit of claim 22 wherein the sheet further includes, for at least some of the medical-procedure tools that are not included in the kit, an unselected end-user selectable field.

24. The kit of claim 1 wherein the sheet further includes an optical code that contains, at least in part, a network address.

25. The kit of claim 24 wherein the network address corresponds to a facility to receive information regarding user selections that have been made as regards the end-user selectable fields.

* * * * *